United States Patent [19]
Knute et al.

[11] Patent Number: 5,932,175
[45] Date of Patent: Aug. 3, 1999

[54] SENSOR APPARATUS FOR USE IN MEASURING A PARAMETER OF A FLUID SAMPLE

[75] Inventors: Wallace L. Knute, deceased, late of Solana Beach, by Joan C. Knute, executrix; David K. Wong, Del Mar; Joseph Y. Lucisano; Thomas J. Carlisle, both of San Diego; Alfonso Del Toro, Chula Vista, all of Calif.

[73] Assignee: Via Medical Corporation, San Diego, Calif.

[21] Appl. No.: 08/719,489

[22] Filed: Sep. 25, 1996

[51] Int. Cl.⁶ .......................... G01N 27/406; G01N 33/48
[52] U.S. Cl. .......................... 422/82.01; 204/415
[58] Field of Search .................. 422/82.01; 204/415, 204/192.17

[56] References Cited

U.S. PATENT DOCUMENTS

| | | | |
|---|---|---|---|
| 4,092,233 | 5/1978 | Clemens et al. | 204/195 P |
| 4,986,271 | 1/1991 | Wilkins | 128/635 |
| 5,266,180 | 11/1993 | Harnoncourt et al. | 204/415 |
| 5,567,302 | 10/1996 | Song et al. | 422/82.01 |

*Primary Examiner*—Lyle A. Alexander
*Attorney, Agent, or Firm*—Sheppard, Mullin, Richter & Hampton LLP; James R. Brueggemann

[57] ABSTRACT

An improved sensor apparatus of a kind that positions a semi-permeable membrane adjacent to an electrode assembly, for measuring a predetermined parameter, e.g., glucose concentration, of an adjacent fluid sample. A special compressible ring serves a first function of tensioning the membrane so that it is maintained in intimate contact with the electrode assembly, and it further serves a second function of sealing the fluid sample from the external environment.

25 Claims, 4 Drawing Sheets

SENSOR APPARATUS FOR USE IN MEASURING A PARAMETER OF A FLUID SAMPLE

BACKGROUND OF THE INVENTION

This invention relates generally to sensor apparatus incorporating semi-permeable membranes, for use in measuring a predetermined parameter of a fluid sample and, more particularly, to sensor apparatus of this kind having means for sealing the fluid sample.

Sensor apparatus of this particular kind are useful in measuring a multitude of parameters of various fluid samples, including for example the measuring of glucose concentration in whole blood. Such sensor apparatus typically include a body or housing having a cavity in which is located an electrode assembly having one or more electrodes and further having a special semi-permeable membrane overlaying the electrodes and separating the electrodes from the fluid sample. The electrodes typically are located on a convex surface of the electrode assembly, and various structures have been used in the past to tension the membrane across the convex surface, in intimate contact with the electrodes. Such intimate contact is important in establishing a rapid response time.

The sensor apparatus described briefly above have, in most instances, functioned satisfactorily in providing reliable measurements of parameters such as glucose concentration in a liquid sample. However, the apparatus are not believed to have been entirely effective in sealing a chamber that carries the sample. This can be a serious deficiency in cases where the sensor apparatus is intended to be stored for an extended period while carrying a particular liquid sample in the chamber, and/or in cases where the chamber must be isolated from the external environment, to maintain the sample's sterility.

It should therefore be appreciated that there is a need for an improved sensor apparatus of the kind that incorporates a semi-permeable membrane overlaying an electrode assembly, for measuring a predetermined parameter of a fluid sample, where the apparatus is configured to more effectively ensure an intimate contact between the membrane and the electrode assembly and where the apparatus is configured to more effectively seal the sample from the external environment. The present invention fulfills this and other needs.

SUMMARY OF THE INVENTION

The present invention is embodied in a sensor apparatus of the kind that incorporates a semi-permeable membrane overlaying an electrode assembly, for measuring a predetermined parameter (e.g., glucose concentration) of a fluid sample, the apparatus more effectively ensuring an intimate contact between the membrane and the electrode assembly and more effectively sealing the fluid sample from the external environment. More particularly, the sensor apparatus includes a body that defines a chamber for carrying the fluid sample, a ring disposed in the body, and a semi-permeable membrane disposed across an opening defined in the ring. An electrode assembly incorporating one or more electrically conductive electrodes is positioned in the ring opening, in intimate contact with the membrane, with the membrane separating the electrode assembly from the fluid sample carried in the chamber. Further, the ring is configured both to tension the membrane and thereby ensure its intimate contact with the electrode assembly, and also to seal the chamber and thereby prevent the escape of the fluid sample.

In a more detailed feature of the invention, the ring has at least limited compressibility, and its opening is substantially circular and centrally located. In addition, the electrode assembly includes a substantially cylindrical projection sized to fit in the ring opening, with the cylindrical projection having a convex surface that engages and tensions the membrane. A mechanism also is included for pressing the electrode assembly against the compressible ring, such that the ring is deformed both axially and radially, to engage a wall of the body and thereby seal the fluid sample in the chamber. The ring preferably has a unitary construction.

In another more detailed feature of the invention, the compressible ring is configured to include an annular irregularity that enhances the sealing of the chamber. In one embodiment, this annular irregularity is a uniform protrusion that faces the electrode assembly and is conformably received in an annular recess or step located in an annular shoulder of the electrode assembly. In this embodiment, the membrane is disposed on the side of the compressible ring facing the electrode assembly, radially inward of the annular protrusion. The compressible ring thus functions to secure the membrane in intimate contact with the electrode assembly and also to provide the seal that prevents the escape of the fluid sample from the chamber. In this embodiment, the ring is formed of a highly compressible elastomeric material such as silicone rubber of soft polyurethane.

In an alternative embodiment of the invention, the ring has a uniform annular recess facing away from the electrode assembly, and the body includes an annular protrusion sized and configured to be conformably received this recess. The membrane is secured to the side of the ring facing away from the electrode assembly, radially outward of the annular recess. This annular recess and annular protrusion cooperate to tension the membrane and ensure its intimate contact with the electrode assembly. In this embodiment, the ring is formed of a more rigid, but nevertheless deformable, plastic material such as hard polyurethane, polycarbonate, or acrylic.

In another more detailed feature of the invention, the body includes a cylindrical wall that defines a cavity sized to receive the electrode assembly, and the sensor apparatus further includes an O-ring disposed in an annular recess defined in a cylindrical wall of the electrode assembly. The O-ring cooperates with the body's cylindrical wall, to provide a further seal that prevents the escape of the fluid sample from the chamber.

Other features of the present invention should become apparent from the following description of the preferred embodiments, taken in conjunction with the accompanying drawings, which illustrate, by way of example, the principles of the invention.

DESCRIPTION OF THE PREFERRED EMBODIMENTS

Figure 1:
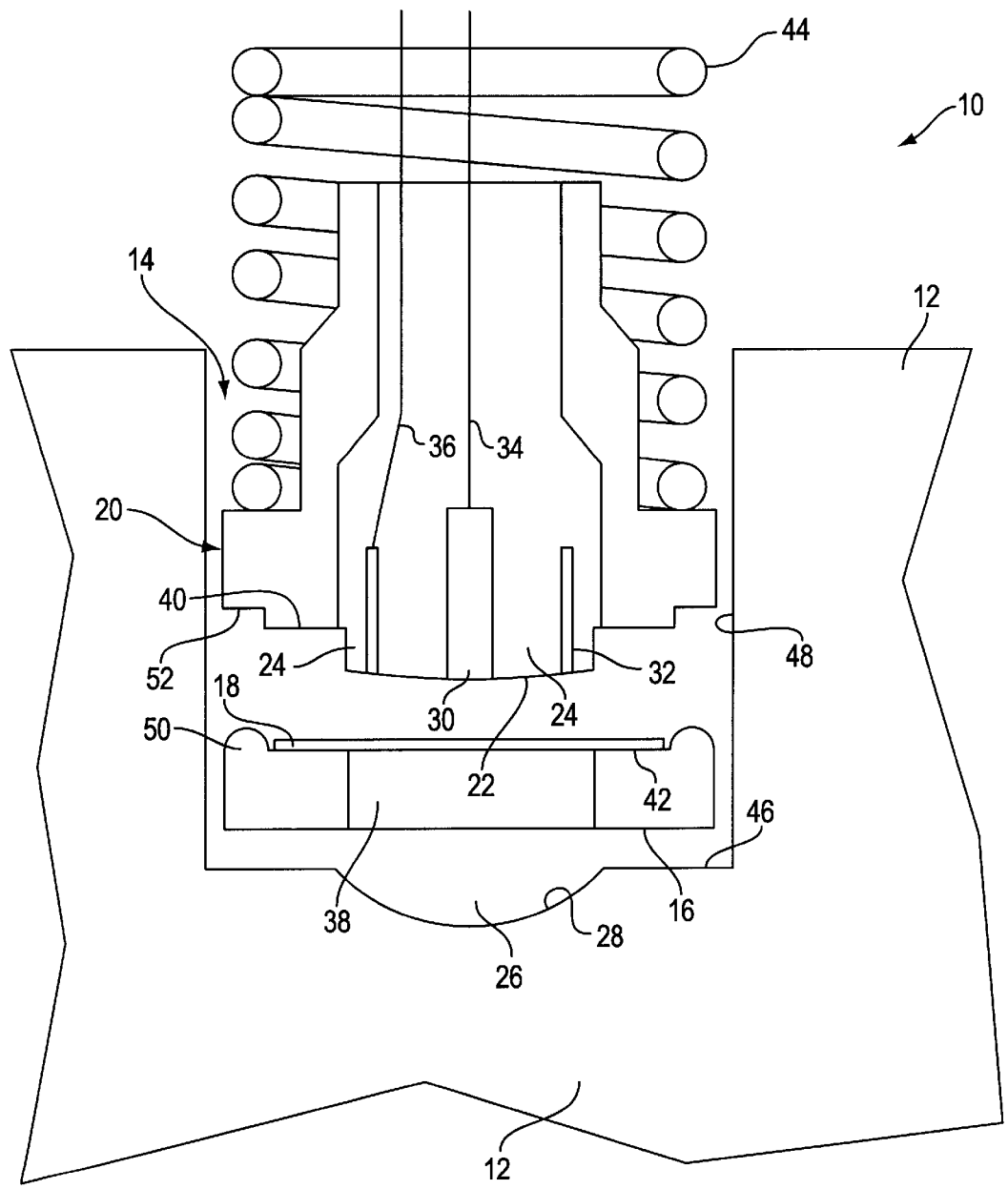
FIG. 1 is an exploded cross-sectional view of a first embodiment of a sensor apparatus that measures the concentration of glucose in a liquid sample.
Figure 2:
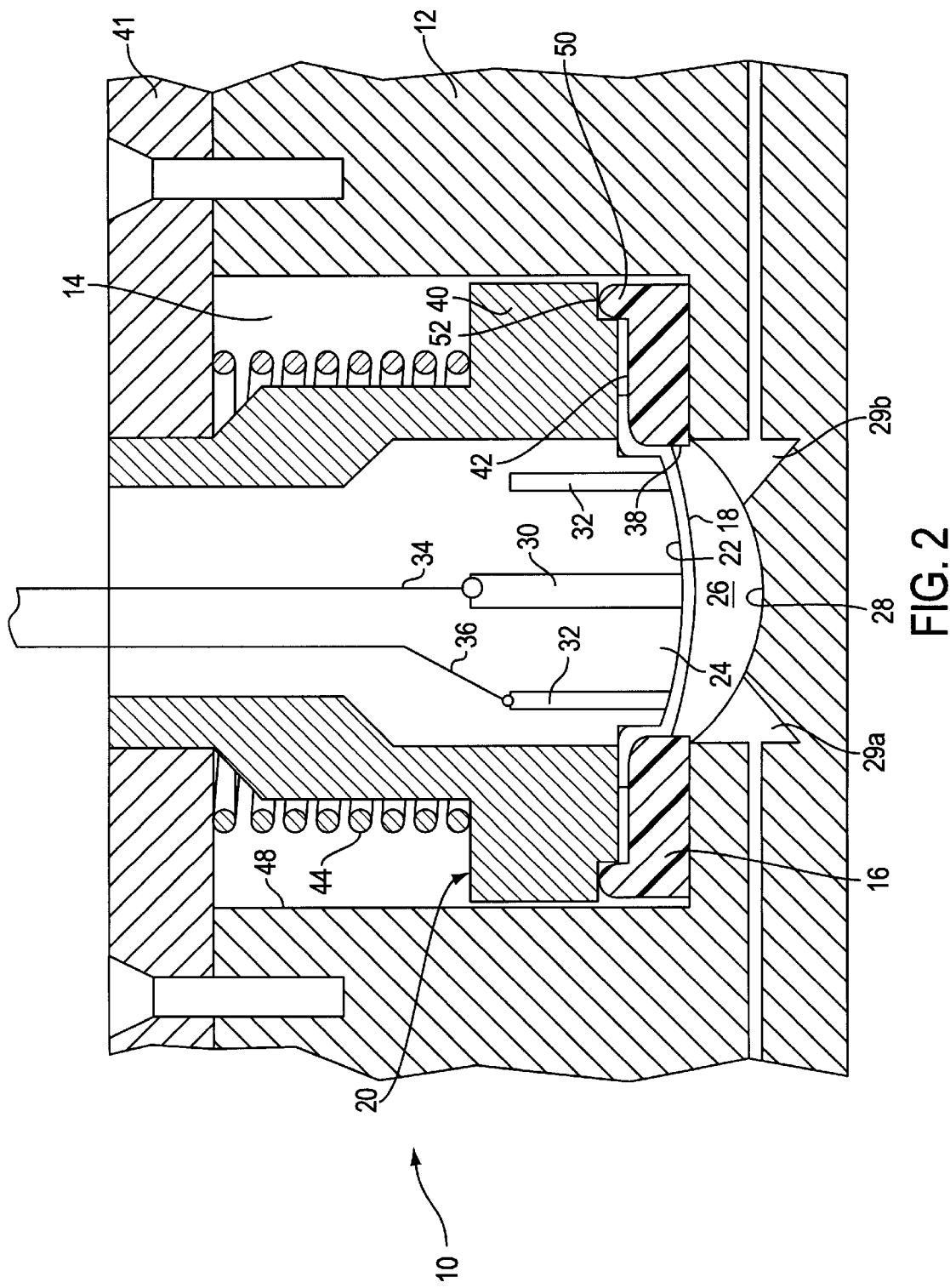
FIG. 2 is a cross-sectional view of the sensor apparatus of FIG. 1, shown in its fully assembled condition.

With reference now to the drawings, and particularly to FIGS. 1 and 2, there is shown a first embodiment 10 of a sensor apparatus for use in measuring the concentration of glucose in a liquid sample such as whole blood. The sensor apparatus includes a plastic body 12 having a generally cylindrical cavity 14 sized to receive a compressible ring 16, a semi-permeable membrane 18, and an electrode assembly 20. When the sensor apparatus is fully assembled, as shown in FIG. 2, the membrane is stretched taut across, and in intimate contact with, a domed or convex surface 22 on a projecting end 24 of the electrode assembly. The membrane separates that surface from a passageway 26 formed by a depression 28 at the lower end of the cavity 14. The liquid sample is channeled through this passageway via inlet and outlet ports 29a and 29b, respectively.

The semi-permeable membrane 18 allows the permeation of glucose and oxygen from the liquid sample, and it incorporates the enzyme glucose oxidase, which acts as a catalyst for a reaction between the glucose and oxygen. This reaction produces hydrogen peroxide, whose concentration is detected by the electrode assembly 20. One suitable glucose membrane is disclosed in copending application for U.S. patent Ser. No. 08/698,045, filed Aug. 16, 1996, in the names of David K. Wong et al., which is incorporated by reference.

The projecting end 24 of the electrode assembly 20 functions as a polarographic anode-cathode assembly that detects the concentration of hydrogen peroxide. It incorporates a central anode 30 and a concentric annular cathode 32, which are encased in an insulating material such as epoxy resin. The anode can be formed of platinum, and the cathode can be formed of silver, although other electrically conductive materials alternatively can be used. The exposed ends of the anode and cathode are flush with the assembly's exposed convex surface 22. Electrical conductors or leads 34 and 36 extend upwardly from the anode 30 and cathode 32, respectively. Each such lead is formed of the same material as is the electrode to which it is attached.

The compressible ring 16 is disposed at the bottom of the cavity 14 formed in the body 12, concentric with the depression 28 that forms the liquid passageway 26. The semi-permeable membrane 18 is supported on the ring's top surface, extending across a circular opening 38 defined in the ring. The projecting end 24 of the electrode assembly 20 has a cylindrical shape that conforms to the ring opening.

During assembly of the sensor apparatus 10, the membrane 18 is engaged by the electrode assembly's projecting end 24 and stretched uniformly across the assembly's convex surface 22 as the projecting end is slid through the ring opening 38. The electrode assembly 20 and the ring 16 are sized such that insertion of the electrode assembly into the ring opening slightly deforms the ring radially outwardly. This frictionally holds the membrane and ensures that it remains in intimate contact with the assembly's convex surface.

The downward, sliding movement of the electrode assembly 20 into the opening 38 formed in the compressible ring 16 ends when an annular shoulder 40 of the assembly reaches the ring's top surface 42. Compression of the electrode assembly against the ring, which is provided by the force of a compression spring 44, clamps the outer periphery of the membrane 18 in place and further ensures that the membrane maintains its intimate contact with the electrode assembly's convex surface 22. The compression spring is located between the backside of the electrode assembly's shoulder 40 and a cap 41. The desired tension in the membrane is provided according to the relative diameters of the electrode assembly's projecting end 24 and the ring opening 38, the height of the projecting end, the thickness of the membrane, and the force of the compression spring.

Compression of the electrode assembly 20 against the compressible ring 16 presses the ring axially against a circular wall 46 of the body 12 that defines the lower end of the cylindrical cavity 14, and it also deforms the ring radially outwardly into compressive engagement with a cylindrical wall 48 of the body. This effectively seals the liquid passageway 26 against the escape of the liquid sample via the space between the body walls and the ring. The ring is formed of a chemically inert material, and preferably a highly compressible elastomeric material such as silicone rubber or soft polyurethane.

The compressible ring 16 incorporates an upwardly projecting annular protrusion 50 at its outer periphery, radially outward of the semi-permeable membrane 18. This protrusion is received in a complementary annular recess or step 52 formed at the outer periphery of the electrode assembly's shoulder 40. When the electrode assembly 20 is compressed against the ring, the protrusion is compressed within the recess or step, much like an O-ring. This seals the membrane and prevents any portion of the liquid sample escaping from the liquid passageway 26 by wicking through the membrane.

Thus, it will appreciated that the compressible ring 16 provides two independent functions. One function is to tension the semi-permeable membrane 18 and thereby ensure that it maintains an intimate contact with the anode 30 and cathode 32 of the electrode assembly's convex surface 22. The other function is to seal the liquid passageway 26, preventing the escape of liquid from the passageway and, in addition, preventing the contamination of the passageway from external sources.

Figure 3:
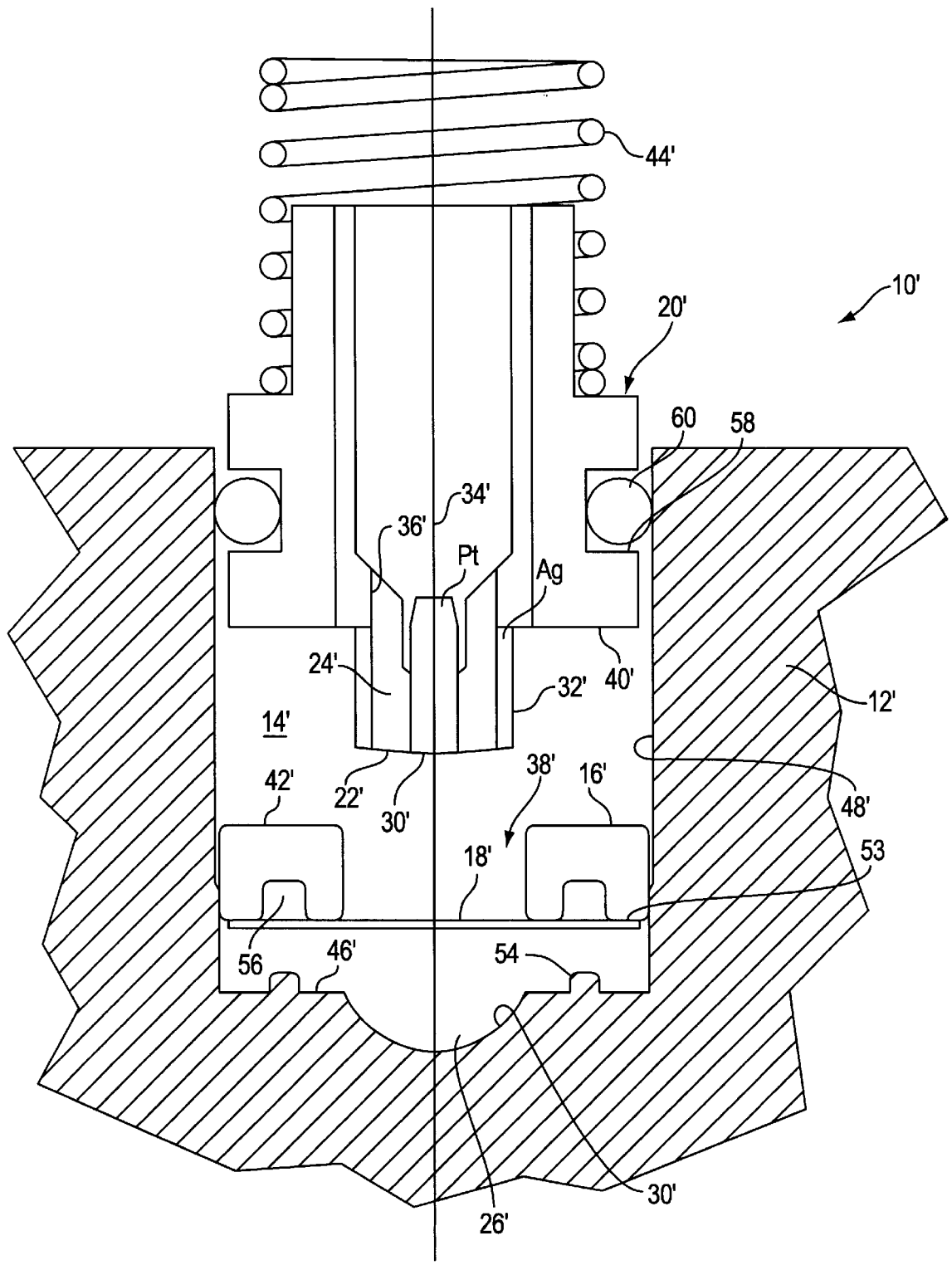
FIG. 3 is an exploded cross-sectional view of a second embodiment of a sensor apparatus that measures the concentration of glucose in a liquid sample.
Figure 4:
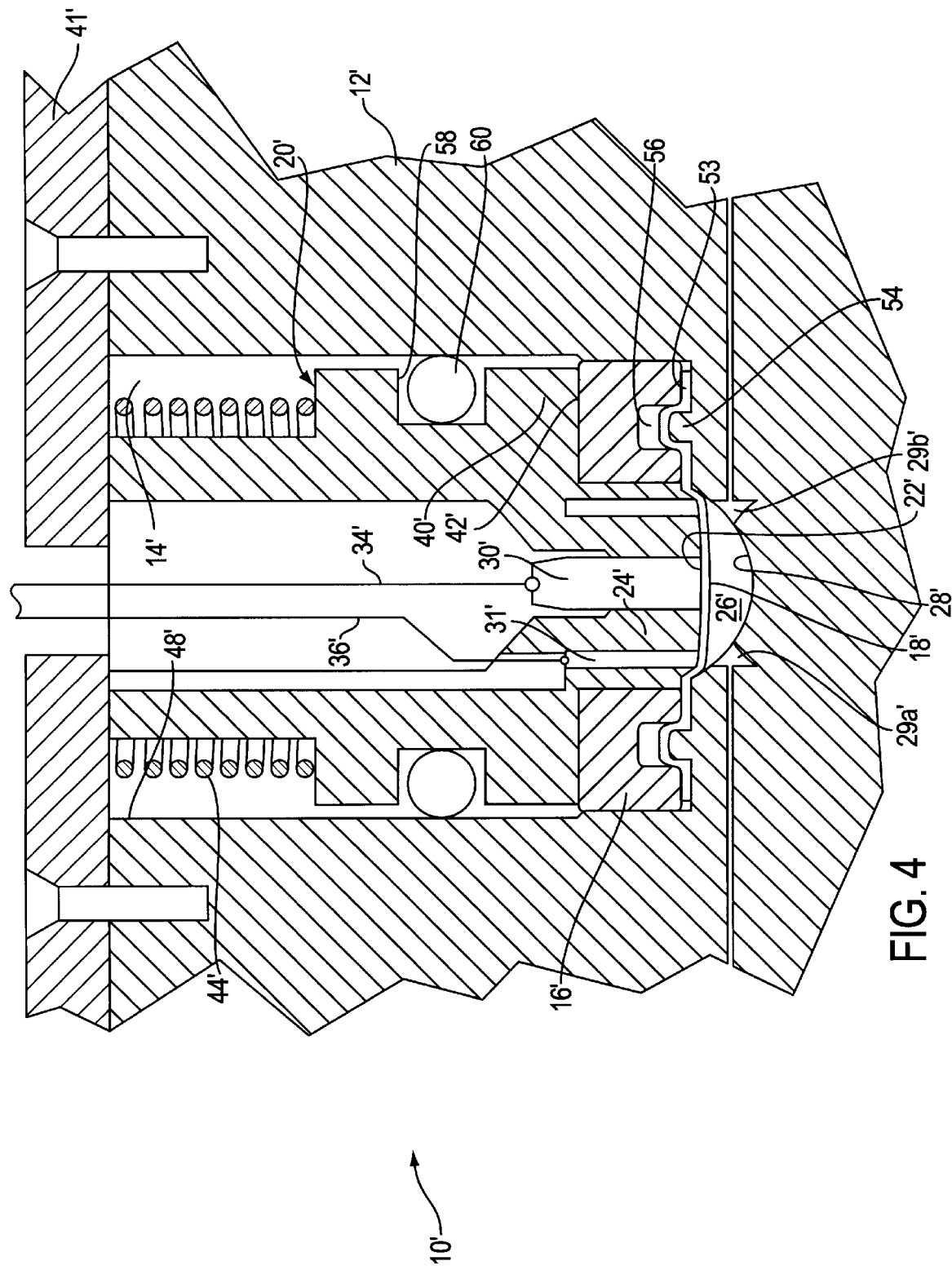
FIG. 4 is a cross-sectional view of the sensor apparatus of FIG. 3, shown in its fully assembled condition.

With reference now to FIGS. 3 and 4 of the drawings, there is shown a second embodiment 10' of a sensor apparatus for use in measuring the concentration of glucose in a liquid sample such as whole blood. Components of the embodiment of FIGS. 3 and 4 that correspond to components of the embodiment of FIGS. 1 and 2 embodiment are identified in the drawings by the same reference numerals, except with an added prime mark.

Like the sensor apparatus 10 of FIGS. 1 and 2, the sensor apparatus 10' of FIG. 3 includes a plastic body 12' that forms a generally cylindrical cavity 14' sized to receive a ring 16', a semi-permeable membrane 18', and an electrode assembly 20'. When the sensor apparatus is fully assembled, the membrane is stretched taut across, and in intimate contact with, a convex surface 22' on a projecting end 24' of the electrode assembly. The membrane separates that surface from a liquid passageway 26' formed by a depression 28' at the lower end of the cavity 14'.

The electrode assembly 10' functions as a polarographic anode-cathode assembly that detects the concentration of hydrogen peroxide. A central anode 30' and a concentric annular cathode 32' are encased in an insulating material such as epoxy resin, and they terminate at the convex surface 22'. Electrical leads 34' and 36' extend upwardly from the anode and cathode, respectively.

In contrast with the embodiment 10 of FIGS. 1 and 2, the semi-permeable membrane 18' of the embodiment 10' of FIGS. 3 and 4 is positioned beneath the ring 16', between the ring and the circular wall 46' at the bottom of the body cavity 14'. The membrane is preliminarily secured to an outer portion 53 of the ring's underside, as for example by ultrasonic welding, heat-staking, or an adhesive. The membrane/ring assembly then is press-fit into in the bottom of the cavity, with an annular ridge 54 formed in the bottom wall conformably engaging an annular recess 56 formed in the ring's underside. The annular ridge and recess mate with an interference fit, to tension the membrane and further secure the membrane in place.

After the ring 16' has been press-fit into its prescribed position, the semi-permeable membrane 18' is held in a taut condition. This is the case even before the electrode assembly 20' has been compressed against the ring. Moreover, this taut condition can be visually inspected, to ensure that it is free of any folds or other irregularities, which could adversely affect the blood glucose measurements to be produced.

Placement of the electrode assembly 20' in the cavity 14' of the body 12', with the projecting end 24' press-fit into the opening 38' of the ring 16', then causes the assembly's convex surface 22' to deflect the semi-permeable membrane 18' downwardly, as shown in FIG. 4. This further tensions the membrane and ensures that its intimate contact with the surface and the anode 30' and cathode 32' is maintained.

Compression of the electrode assembly 20' against the ring 16', provided by the force of a compression spring 44', presses the electrode assembly 20' and the ring against the underlying membrane 18' and against the bottom, circular wall 46' of the body cavity 14'. This action, in conjunction with the press-fitting of the ring/membrane assembly, effectively seals the liquid passageway 26' that carries the blood sample to be tested. The compressed ring also prevents the escape of any blood components that might wick along the membrane.

In this embodiment, the ring 16' is formed of a somewhat more rigid plastic material such as hard polyurethane, polycarbonate or acrylic. The ring is sized to provide an interference fit with both the cylindrical wall 48' of the body 12' and also the projecting end 24' of the electrode assembly 20'. Accordingly, only limited axial and radial deformation of the ring is required to provide the desired fluid seal.

Thus, as was the case in the sensor apparatus 10 of FIGS. 1 and 2, the ring 16' of the sensor apparatus 10' of FIG. 3 provides two independent functions. One function is to tension the semi-permeable membrane 18' and thereby ensure that it maintains an intimate contact with the anode 30' and cathode 32' of the electrode assembly's convex surface 22'. The other function of the ring is to seal the liquid passageway 26', both to prevent the escape of liquid from the passageway and to prevent the contamination of the passageway from external sources.

The outer, cylindrical surface of the electrode assembly 20' incorporates an annular recess 58, in which is positioned an O-ring 60 for engaging the cylindrical wall 48' that defines the body cavity 14'. This further seals the liquid passageway 26', to prevent the escape of liquid from the passageway and to prevent external contaminants from reaching the passageway. This O-ring construction also can be incorporated as a secondary seal in the embodiment of FIGS. 1 and 2.

It should be appreciated from the foregoing description that the present invention provides an improved sensor apparatus of a kind that positions a semi-permeable membrane adjacent to an electrode assembly, for measuring the concentration of a particular component of an adjacent liquid sample. A special compressible ring serves a first function of tensioning the membrane so that it maintains an intimate contact with the electrode assembly, and further serves a second function of sealing the liquid sample. The apparatus is of simple construction, and it is manufactured inexpensively and in a repeatable manner.

Although the invention has been described in detail with reference only to the presently preferred embodiments, those skilled in the art will appreciate that various modifications can be made without departing from the invention. Accordingly, the invention is defined only by the following claims.

We claim:

1. Sensor apparatus for use in measuring a predetermined parameter of a fluid sample, comprising:

a body defining a chamber for carrying the fluid sample;

a ring disposed in the body, the ring defining an opening adjacent to the chamber;

a semi-permeable membrane disposed across the opening defined in the ring; and an electrode assembly incorporating one or more electrically conductive electrodes, at least a portion of the electrode assembly being positioned in the opening defined in the ring, in intimate contact with the membrane;

wherein the membrane separates the electrode assembly from the fluid sample in the chamber;

and wherein the ring is configured both to tension the membrane and thereby ensure its intimate contact with the electrode assembly, and to seal the chamber and thereby prevent the escape of the fluid sample.

2. Sensor apparatus as defined in claim 1, wherein:

the ring has at least limited compressibility, and the opening defined in the ring is substantially circular and centrally located; and the electrode assembly includes a substantially cylindrical projection sized to fit in the ring opening, the cylindrical projection having a convex surface that engages and further tensions the membrane.

3. Sensor apparatus as defined in claim 2, wherein the ring includes an annular irregularity that provides the seal that prevents the escape of the fluid sample from the chamber.

4. Sensor apparatus as defined in claim 3, wherein:

the annular irregularity of the ring is an annular protrusion facing the electrode assembly and having a substantially uniform height;

the electrode assembly includes an annular shoulder encircling the substantially cylindrical projection and including an annular recess sized and configured to receive the annular protrusion of the ring;

the membrane is disposed on the side of the ring facing the electrode assembly, radially inward of the annular protrusion; and the annular protrusion of the ring and the annular recess of the electrode assembly cooperate to provide the seal that prevents the escape of the fluid sample from the chamber.

5. Sensor apparatus as defined in claim 3, wherein the ring has a unitary structure and is formed of a material selected from the group consisting of silicone rubber and soft polyurethane.

6. Sensor apparatus as defined in claim 2, wherein:

the ring includes an annular recess facing away from the electrode assembly and having a substantially uniform depth;

the body includes an annular protrusion sized and configured to be received by the annular recess defined in the ring;

the membrane is disposed on the side of the ring facing away from the electrode assembly; and the annular recess of the ring and the annular protrusion of the body cooperate to tension the membrane and ensure its intimate contact with the electrode assembly.

7. Sensor apparatus as defined in claim 2, wherein:

the body includes a wall that defines a cavity sized to receive the ring with a press-fit; and the opening of the ring is sized to receive the cylindrical projection of the electrode assembly with a press-fit.

8. Sensor apparatus as defined in claim 7, wherein the ring has a unitary structure and is formed of a material selected from the group consisting of hard polyurethane, polycarbonate and acrylic.

9. Sensor apparatus as defined in claim 2, wherein:

the body includes a wall that defines a substantially cylindrical cavity sized to receive the ring with a press-fit; and the sensor apparatus further includes a mechanism for compressing the electrode assembly against the ring, to provide the seal that prevents the escape of the fluid sample from the chamber.

10. Sensor apparatus as defined in claim 1, wherein:

the body includes a cylindrical wall that defines a cavity sized to receive the electrode assembly;

the electrode assembly further includes an outer, cylindrical wall that defines an annular recess; and the sensor apparatus further includes an O-ring disposed in the annular recess defined in the cylindrical wall of the electrode assembly, to cooperate with the cylindrical wall defined in the body, to provide a further seal that prevents the escape of the fluid sample from the chamber.

11. Sensor apparatus as defined in claim 1, wherein:

the sensor apparatus is used to measure the concentration of glucose in the fluid sample; and the semi-permeable membrane incorporates glucose oxidase.

12. Sensor apparatus as defined in claim 1, wherein the electrode assembly includes:

a first electrode and an associated electrical lead, both formed of a first precious metal; and a second electrode and an associated electrical lead, both formed of a second precious metal.

13. Sensor apparatus for use in measuring a predetermined parameter of a fluid sample, comprising:

a body defining a chamber for carrying the fluid sample;

an electrode assembly that carries one or more electrically conductive electrodes;

a ring disposed in the body, adjacent to the chamber, the ring defining an opening; and a semi-permeable membrane disposed across the opening defined in the ring;

wherein the electrode assembly is sized to fit through the opening defined in the ring, to engage and tension the membrane, the tensioned membrane intimately contacting the electrode assembly and separating the electrode assembly from the fluid sample in the chamber; and wherein the ring is configured to provide a seal in a region radially beyond the tensioned membrane, to prevent the escape of the fluid sample from the chamber.

14. Sensor apparatus as defined in claim 13, wherein:

the ring has at least limited compressibility, and the opening defined in the compressible ring is substantially circular and centrally located; and the electrode assembly includes a substantially cylindrical projection sized to fit in the opening defined by the compressible ring, the cylindrical projection having a convex surface that engages and tensions the membrane.

15. Sensor apparatus as defined in claim 14, wherein the compressible ring includes an annular irregularity that provides the seal that prevents the escape of the fluid sample from the chamber.

16. Sensor apparatus as defined in claim 15, wherein:

the annular irregularity of the compressible ring is an annular protrusion facing the electrode assembly and having a substantially uniform height;

the electrode assembly includes an annular shoulder encircling the substantially cylindrical projection and including an annular recess sized and configured to receive the annular protrusion of the compressible ring;

the membrane is disposed on the side of the compressible ring facing the electrode assembly; and the annular protrusion of the compressible ring and the annular recess of the electrode assembly cooperate to provide the seal that prevents the escape of the fluid sample from the chamber.

17. Sensor apparatus as defined in claim 15, wherein the compressible ring has a unitary structure and is formed of a material selected from the group consisting of silicone rubber and soft polyurethane.

18. Sensor apparatus as defined in claim 14, wherein:

the ring includes an annular recess facing away from the electrode assembly and having a substantially uniform depth;

the body includes an annular protrusion sized and configured to be received by the annular recess defined in the compressible ring;

the membrane is disposed on the side of the compressible ring facing away from the electrode assembly, radially inward of the annular recess; and the annular recess of the compressible ring and the annular protrusion of the body cooperate to tension the membrane and ensure its intimate contact with the electrode assembly.

19. Sensor apparatus as defined in claim 14, wherein:

the body includes a wall that defines a cavity sized to receive the compressible ring with a press-fit; and the opening of the compressible ring is sized to receive the cylindrical projection of the electrode assembly with a press-fit.

20. Sensor apparatus as defined in claim 19, wherein the ring has a unitary structure and is formed of a material selected from the group consisting of hard polyurethane, polycarbonate and acrylic.

21. Sensor apparatus as defined in claim 14, wherein:

the body includes a wall that defines a substantially cylindrical cavity sized to receive the ring with a press-fit; and the sensor apparatus further includes a mechanism for compressing the electrode assembly against the ring, to provide the seal that prevents the escape of the fluid sample from the chamber.

22. Sensor apparatus as defined in claim 14, wherein:

the body includes a cylindrical wall that defines a cavity sized to receive the electrode assembly;

the electrode assembly further includes an outer, cylindrical wall that defines an annular recess; and the sensor apparatus further includes an O-ring disposed in the annular recess defined in the cylindrical wall of the electrode assembly, to cooperate with the cylindrical wall defined in the body, to provide a further seal that prevents the escape of the fluid sample from the chamber.

23. Sensor apparatus as defined in claim 13, wherein:

the sensor apparatus is used to measure the concentration of glucose in the fluid sample; and the semi-permeable membrane incorporates glucose oxidase.

24. Sensor apparatus as defined in claim 13, wherein the electrode assembly includes:

a first electrode and an associated electrical lead, both formed of a first precious metal; and a second electrode and an associated electrical lead, both formed of a second precious metal.

25. Sensor apparatus for measuring the concentration of glucose in a fluid sample, comprising:

a body having a wall that defines a generally cylindrical cavity, with a depression at one end of the cavity defining a passageway for carrying the fluid sample;

an elastomeric ring, of unitary construction, disposed in the body cavity, the ring defining a circular opening disposed adjacent to the passageway, and the ring further defining an annular protrusion around its periphery, the protrusion having a substantially uniform height;

a semi-permeable membrane disposed across the ring opening, radially inward of the annular protrusion;

an electrode assembly incorporating one or more electrically conductive electrodes, the electrode assembly including a substantially cylindrical projection sized to fit in the ring opening, and further including an annular shoulder encircling the cylindrical projection and defining an annular recess sized and configured to conformably receive the annular protrusion of the ring;

wherein the cylindrical projection of the electrode assembly defines a convex surface; and a mechanism for compressing the electrode assembly against the elastomeric ring, such that the convex surface of the electrode assembly engages and intimately contacts the membrane, the membrane separating the electrode assembly from the fluid sample in the passageway, and such that the ring is deformed radially outwardly to engage the body wall, to seal the chamber and thereby prevent the escape of the fluid sample from the chamber.

* * * * *